United States Patent [19]

Deisenroth et al.

[11] Patent Number: 5,708,119

[45] Date of Patent: Jan. 13, 1998

[54] PERFLUOROALKYL SULFIDE, SULFONE, POLYSULFONE AND POLYSULFIDE DIOLS

[75] Inventors: Ted Deisenroth, Carmel, N.Y.; Marlon Haniff, West Orange, N.J.

[73] Assignee: Ciba Specialty Chemicals Corporation, Tarrytown, N.Y.

[21] Appl. No.: 665,125

[22] Filed: Jun. 14, 1996

Related U.S. Application Data

[62] Division of Ser. No. 270,067, Jul. 1, 1994, abandoned.

[51] Int. Cl.$^6$ .............................. C08G 18/28; C08G 18/70
[52] U.S. Cl. .................................. 528/70; 528/44; 528/65; 528/87; 528/321; 528/401; 528/422; 528/495; 528/499; 528/503; 560/227
[58] Field of Search ........................... 528/44, 65, 70, 528/87, 321, 401, 432, 495, 499, 503; 560/227

[56] References Cited

U.S. PATENT DOCUMENTS 4,946,992  8/1990  Falk et al. ............................... 560/227

OTHER PUBLICATIONS

Journal of Fluorine Chemistry 51(1991) 43–52 "Synthetic Utility of 3–(Perfluoro–1,1–dimethylbutyl) 1–propene" Halina Plen Kiewicz et al.

*Primary Examiner*—James J. Seidleck
*Assistant Examiner*—Duc Truong
*Attorney, Agent, or Firm*—Kevin T. Mansfield

[57] ABSTRACT

Bisperfluoroalkyl-substituted diols containing sulfide, sulfone or polysulfide linkages and a method for making them are described. These diols can react with isocyanates to form urethanes; diisocyanates to form polyurethanes; chloroformates to form carbonates; with carboxylic, sulfuric or phosphoric acids or derivatives to form carboxylate esters, sulfate esters, phosphate esters respectively. These diol compounds and their derivatives are useful for imparting oil and water repellency to substrates such as glass, wood, paper, leather, wool, cotton, polyester and other substrates.

4 Claims, No Drawings

PERFLUOROALKYL SULFIDE, SULFONE, POLYSULFONE AND POLYSULFIDE DIOLS

This application is a Division of Ser. No. 08/270,067 filed Jul. 5, 1994 now abandoned.

BACKGROUND OF THE INVENTION

This invention relates to bisperfluoroalkyldiols and their derivatives which impart oil water repellency on materials such as glass, wood, paper, leather, wool, cotton, polyester and other substrates.

Perfluoroalkyl-substituted polymers possess free surface energies even lower than that of poly-tetrafluoroethylene (Teflon). They have therefore long been used to impart oil- and water repellency to a wide variety of substrates, especially textiles. Phosphate esters of perfluoroalkyl-substituted alcohols are also being used as oil- and water repellent paper sizes, for instance in paper plates and in food packaging products. In these applications it is especially important that the paper sizing compound contain at least two perfluoroalkyl or $R_F$ groups. When mono-$R_F$ alcohols are used to esterify phosphoric acid, only the diesters are active oil- and water repellents. The monoester is too water soluble and, even if retained on the cellulose fiber, reduces water repellency, and the triester is not substantive. However making phosphate diesters in high yield is very difficult in practice; substantial amounts of mono- and triesters are always produced as by products. It is also impossible to prepare oil-and water-repellent paper sizes in form of sulfuric acid half-esters from mono-$R_F$ alcohols, since such esters are very water soluble anionic surfactants and have a detrimental effect on water repellency. Mono-$R_F$-substituted alcohols and diols, though suitable for the preparation of acrylic and methacrylic oil- and water-repellent $R_F$-polymers, are therefore less suitable for the preparation of oil-repellent phosphate or sulfate ester acidic paper sizes.

The use of di-$R_F$-substituted alcohols and diols makes it possible to prepare highly oil-repellent phosphate or sulfate monoester paper sizes, since even a mono-ester contains two $R_F$ groups. This approach and some such compounds are described in U.S. Pat. Nos. 5,091,550 and 5,132,445.

For the preparation of oil- and water-repellent polyurethanes it is especially important that the diol contain more than one $R_F$ group. Cemin such diols and polyurethanes thereof are described in U.S. Pat. Nos. 3,935,277; 3,968,066; 4,046,944; 4,054,592; 4,098,742; 4,946,992 and 5,200,493.

Although the di-$R_F$-substituted phosphates and $R_F$-substituted polyurethanes described in the above patents show excellent performance, the synthesis of the bisperfluoroalkyl-substituted diols involve many steps and costly intermediates such as $R_F$-ethylenethiols and halogenated alcohols and diols. Copending application Ser. No. 08/420,386, now U.S. Pat. No. 5,585,517 describes bisperfluoroalkyl-substituted diols produced by a more straightforward synthesis route, namely by direct addition of perfluoroalkyl iodides ($R_F$I) to diallyl diols, followed by elimination of HI with a base. Another synthetic mute to di-$R_F$-diols is described in J. Fluorine Chemistry, 62, (1993), p. 161–171. It involves the dimerization of $R_F$I/allyl acetate adducts with zinc. The yields are less than 60% and numerous by-products are formed.

It has now been discovered that bisperfluoroalkyl-substituted diols can be synthesized in high yield and purity by reaction of an $R_F$-substituted epoxide with sulfide ions in the presence of a base. These novel diols, containing sulfide, polysulfide, sulfone, polysulfone and di-thioether moieties, have not been previously reported. They are useful for synthesizing perfluoroalkyl-substituted urethanes, polyurethanes, carboxylate esters and acids, polyesters, sulfate esters and acids, phosphate esters and acids, and carbonate esters and acids. These compounds are isolated in high yield and purity.

Some dicarboxylic acids, their metal salts and lower alkyl esters which contain two polyfluoroalkoxyalkyl carboxy moieties joined by —S— or a —S—alkylene—S— crosslink have been reported in U.S. Pat. No. 3,828,098. Also, certain structures of the type $R_F$-$S_x$-$R'_F$ have been reported in U.S. Pat. No. 3,700,646, where $R_F$ and $R'_F$ are polyfluoroisoalkoxyalkyl radicals and x is 1 to 8. Such materials would be difficult to derivatize without significant functional group transformations.

DETAILED DISCLOSURE

The new bisperfluoroalkyldiols are of the formula I

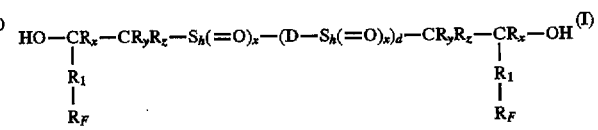

wherein
$R_1$ is a direct bond, a branched or linear alkylene of up to 6 carbon atoms, alkyleneoxyalkylene of up to 6 carbon atoms, alkylenethioalkylene of up to 6 carbon atoms, alkyleneoxy of up to 6 carbon atoms, alkenyleneoxyalkylene of up to 6 carbon atoms, alkylenethioalkyleneoxyalkylene of up to 9 carbon atoms, carbonamidoalkylene where the alkylene moiety contains up to 6 carbon atoms and the amido nitrogen is unsubstituted or further substituted by lower alkyl, sulfonamidoalkldyene wherein the alkylene moiety contains up to 6 carbon atoms and the amido nitrogen is unsubstituted or further substituted by lower alkyl; carbonamidoalkylenethioalkylene wherein the carbonamidoalkylene moiety is as defined hereinabove and the thioalkylene moiety contains up to 6 carbon atoms, or sulfonamidoalkylenethioalkylene wherein the sulfonamidoalkylene moiety is as defined hereinabove and the thioalkylene moiety contains up to 6 carbon atoms, $R_x$, $R_y$ and $R_z$ are independently of each other alkyl groups with 1–5 carbon atoms or hydrogen, h is 1 or 2, x is 0, 1, or 2, with the proviso that when h is 2, x is 0, d is 0 or 1, D is an alkylene group with 2 to 10 carbon atoms, a dialkylene ether group with 4 to 10 carbon atoms, or pentaerythritol diacetate or dipropionate, and $R_F$ is a monovalent, perfluorinated, alkyl or alkenyl, straight, branched or cyclic, organic radical having 3 to 20 fully fluorinated carbon atoms, which radical can be interrupted by one or more divalent oxygen or sulfur atoms, and each $R_F$ radical is the same or different.

By lower alkyl is meant $C_1$-$C_5$alkyl.

Preferred are compounds wherein $R_x$ is a direct bond, —$CH_2$—, —$CH_2CH_2$—O—$CH_2$—, —$CH(CH_3)$—, —$CH_2CH_2$—S—$CH_2$—, —CH=CHCH$_2$—O—$CH_2$—, —$SO_2NR_o$—$CH_2$— or —CONH—$CH_2CH_2$—O—$CH_2$—, wherein $R_o$ is hydrogen or an alkyl group with 1 to 4 carbon atoms, $R_x$ is methyl or hydrogen, $R_y$ and $R_z$ are hydrogen, h is 1, x and d are zero and the $R_F$ group is saturated, contains 6–18 carbon atoms, is fully fluorinated and contains at least one terminal perfluoromethyl group.

Also preferred are compounds wherein $R_1$ is a direct bond, —$CH_2$—, —$CH_2CH_2$—O—$CH_2$—, —$CH_2CH_2$—

S—CH$_2$—, —CH=CHCH$_2$—O—CH$_2$—, —SO$_2$NR$_o$—CH$_2$— or —CONH—CH$_2$CH$_2$—O—CH$_2$—, R$_x$ is methyl or hydrogen, R$_y$ and R$_z$ are hydrogen, h is 1, x is 2, d is zero, and the R$_F$ group is saturated, contains 4–18 carbon atoms, is fully fluorinated and contains at least one terminal perfluoromethyl group.

Also preferred are compounds wherein R$_x$ is a direct bond, —CH$_2$—, —CH$_2$CH$_2$—O—CH$_2$—, —CH$_2$CH$_2$—S—CH$_2$—, —CH=CHCH$_2$—O—CH$_2$—, —SO$_2$NR$_o$—CH$_2$— or —CONH—CH$_2$CH$_2$—O—CH$_2$—, R$_x$ is methyl or hydrogen, R$_y$ and R$_z$ are hydrogen, h and d are 1, x is zero, D is —CH$_2$CH$_2$—O—CH$_2$CH$_2$— or pentaerythritol diacetate or dipropionate and the R$_F$ group is saturated, contains 4–18 carbon atoms, is fully fluorinated and contains at least one terminal perfluoromethyl group.

Most preferably, R$_1$ is —CH$_2$—, R$_x$, R$_y$ and R$_z$ are hydrogen, h is 1, x and d are zero and R$_F$ is a fully fluorinated, linear perfluoroalkyl group with 4 to 14 carbon atoms.

It is understood that the R$_F$ group usually represents a homologous mixture of perfluoroalkyl moieties. That is, an R$_F$ group indicated as containing a certain number of carbon atoms will also contain a small fraction of perfluoroalkyl groups with fewer carbon atoms and a small fraction of perfluoroalkyl groups with a higher number of carbon atoms. Ordinarily, the perfluoroalkyl group preferably contains a mixture of C$_4$F$_9$—, C$_6$F$_{13}$—, C$_8$F$_{17}$—, C$_{10}$F$_{21}$—, C$_{12}$F$_{25}$— and C$_{14}$F$_{29}$— radicals.

The novel diols of this invention where x is 0 are made by reaction of an R$_F$-R$_1$-substituted epoxide with Na$_2$S or NaHS, resulting in thioether diols, with elemental sulfur, Na$_2$S$_4$ or Na$_2$S$_5$ to form polysulfide diols, or with an organic dithiol to form di-thioether diols. Sulfoxides and sulfones (x is 1 or 2) can be prepared by oxidizing the corresponding thioethers with, for example, 1 or 2 equivalents of an oxidizing agent, preferably a peroxide, per sulfide linkage.

The diol-forming reaction is advantageously carried out in the presence of water and an organic diluent or solvent. Said organic diluent or solvent should be low boiling enough to be recoverable by distillation, including vacuum distillation, if desired. Typical useful diluents and solvents are ketones, such as methyl propyl ketone, methyl ethyl ketone or acetone; esters such as ethyl acetate or isopropyl acetate, and alcohols such as ethanol, n-propanol, isopropanol, n-, sec.- or tert.-butanol or allyl alcohol. Typical reaction temperatures are 40° to 80° C. and reaction times are 1 to 8 hours.

Typical R$_F$-epoxides are of the formula R$_F$-R$_1$-EP, wherein EP denotes an epoxy group, —CH(—O—)CH$_2$, and R$_F$ and R$_1$ are defined as above. Said compounds are known per se or can be prepared by known methods. For example some such epoxides are described in U.S. Pat. Nos. 4,038,195; 4,435,330; 4,490,304 and 4,577,036.

Preferred are epoxides of the formulae R$_F$-EP; R$_F$—CH$_2$-EP; R$_F$—CH$_2$CH$_2$—S—CH$_2$-EP; R$_F$—CH$_2$CH$_2$—O—CH$_2$-EP, R$_F$-CH=CHCH$_2$—O—CH$_2$-EP, R$_F$—SO$_2$NR$_o$—CH$_1$-EP, R$_F$—CONH—CH$_2$CH$_2$—O—CH$_2$-EP, with R$_F$CH$_2$-EP being the most preferred.

It has been unexpectedly found that, instead of making the novel di-R$_F$-diols from alpoxides, the halohydrin precursors of the formula

can be used, wherein R$_v$, R$_x$, R$_y$, and R$_z$ are hydrogen or C$_1$-C$_5$alkyl, and hal is bromide or iodide, preferably iodide. The synthesis of diols of the formula Ia

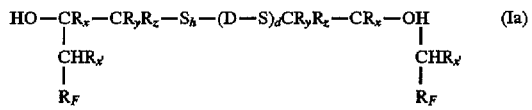

wherein R$_F$, R$_v$, R$_x$, R$_y$, R$_z$, h and d are as defined above, by reaction of

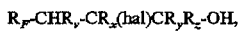

wherein hal is bromide or iodide, with Na$_2$S, Na$_2$S$_4$ or an organic dithiol of the formula HS-D-SH, wherein D is defined as above, in a basic aqueous medium, is thus another embodiment of this invention. Suitable bases for the basic aqueous medium are alkali metal hydroxides such as sodium and potassium hydroxide.

In the preferred halohydrins, R$_v$ and R$_x$ are hydrogen or methyl, R$_y$ and R$_z$ are hydrogen and hal is iodine, with R$_v$ and R$_x$ also as hydrogen being most preferred.

The most preferred di-R$_F$-R$_F$-diol is heptane-1,7-di-perfluoroalkyl-4-thia-2,6-diol. It can be prepared in one reactor by 1) addition of an R$_F$-iodide to allyl alcohol to form the iodohydrin, followed by 2) reaction of the iodohydrin with a sulfide. The epoxide of the formula RF-CH$_2$-EP is formed in low concentrations as an intermediate during the second step, but does not accumulate as an isolatable compound and is not present in the reaction product. The process of making the preferred diols by reaction of 2 moles of a 2-iodo-3-perfluoroalkyl-1-propanol with one mole of a sulfide is another embodiment of this invention.

The addition of an R$_F$-iodide to allyl alcohol to give an iodohydrin intermediate proceeds readily in the presence of a free radical initiator such an azo compound or a peroxide at conventional initiation temperatures of 35° to 150° C. It was found, however, that only in the presence of small amounts of aqueous solutions of sulfite, bisulfite or dithionite ions does the reaction proceed fast enough and are conversions high enough to make the synthesis commercially practical. This novel process to make the R$_F$-iodide-allyl alcohol iodohydrin intermediate and other related compounds is described separately in copending application Ser. No. 08/420,386, now U.S. Pat. No. 5,585,517.

Solvents can be present during this step; for example ketones such as acetone, methyl ethyl ketone or methyl propyl ketone, esters such as isopropyl acetate, alcohols such as ethanol or butanol, ethers such as dioxane or di-(2-hydroxyethyl)-ether, hydrocarbons such as toluene or octane, amides such as dimethylformamide and lactams such as N-methylpyrrolidone.

In the second step the iodohydrin intermediate, a 2-iodo-3-perfluoroalkyl-1-propanol, is reacted with Na$_2$Sx9H$_2$O in the presence of water and an organic diluent or solvent to give a heptane-1,7-di-perfluoroalkyl-4-thia-2,6-diol. Typical diluents and solvents are ketones, such as methyl propyl ketone, methyl ethyl ketone or acetone; esters such as ethyl acetate or isopropyl acetate; alcohols such as ethanol, n-propanol, isopropanol, n-, sec.- or tert. butanol or allyl alcohol. Preferably the same solvent is used as for the previous step. Typical reaction temperatures are 40° to 80° C. and reaction times are 1 to 8 hours.

The key step is the in-situ preparation of a 3-perfluoroalkyl-1,2-epoxypropane as a transitory, non-isolatable intermediate. Evidence of a 3-perfluoroalkyl-1,2-epoxypropane being an intermediate is shown in Example 2. In said example, a 3-perfluoroalkyl-1,2-epoxypropane is converted to heptane-1,7-di-perfluoroalkyl-4-thia-2,6-diol using Na$_2$Sx9H$_2$O. The same novel diols can also be prepared by the addition of NaHS to a 2-iodo-3-perfluoroalkyl-1-propanol.

Instead of allyl alcohol, methallyl alcohol or crotyl alcohol can be used to prepare analogous diols of the formula Ia.

Disulfides and polysulfides of formula (I) can be prepared from the reaction of $Na_2S$ plus elemental sulfur or just elemental sulfur with an $R_F$-iodide at elevated temperatures. $Na_2S_4$ and/or $Na_2S_5$ may also be utilized. These reagents will give a mixture of sulfide and polysulfide structures of formula I, ranging from 1 to 4 sulfur atoms in the cross linkage.

The sulfides and polysulfides of formula I may be oxidized to the corresponding sulfoxides and polysulfoxides or to sulfones and polysulfones. This functional group transformation may be accomplished by the addition of one equivalent of an oxidizing agent, preferably a peroxide, per sulfide linkage or two or more equivalents to give, respectively, sulfoxide/polysulfoxide or sulfone/polysulfone structures of formula I.

Di-thioether diols of formula I can be prepared by reaction of a 2-iodo-3-perfluoroalkyl-1-propanol or an $R_F$-substituted epoxide with a dithiol, for example dimercaptoethylene or pentaerythritol dimercaptopropionate.

The diols of formula I can be further reacted with isocyanates to form urethanes; diisocyanates to form polyurethanes; with carboxylic, sulfuric or phosphoric acids or derivatives to form carboxylate esters, sulfate esters, phosphate esters, or carbonates, respectively. Use of these reaction products and their further derivatives impart oil and water repellency to materials such as glass, wood, paper, leather, textiles such as wool, cotton, polyester and other substrates is another object of this invention.

Useful esters are mono- and diesters of the formula IIa or IIb

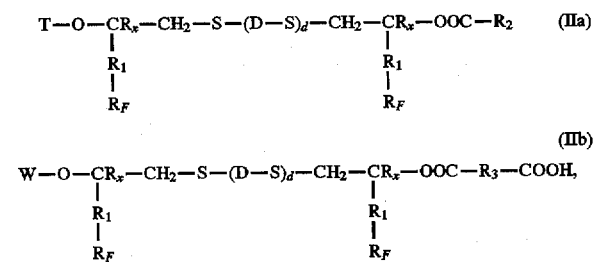

wherein $R_F$, $R_1$, $R_x$, D, and d are defined as above, T is hydrogen or $R_2$—CO—, where $R_2$ is $C_1$–$C_{20}$alkyl, $C_6$–$C_{14}$aryl or $C_7$–$C_{16}$aralkyl, each of which is unsubstituted or substituted by one or more hydroxy, thiol, carboxyl or $C_1$-$C_4$alkyl ester groups and W is hydrogen or HOOC—$R_3$—CO—, where $R_3$ is a direct bond, an alkylene of 1–16 carbon atoms, an arylene of 6 to 14 carbon atoms or an alkarylene of 7 to 16 carbon atoms, which alkylene, arylene or alkarylene is unsubstituted or substituted by $C_1$-$C_4$alkyl, chlorine or bromine.

Structurally, $R_2$ is the radical residue of a carboxylic acid of the formula $R_2$—COOH. Typical examples of $R_2$—COOH include acetic, benzoic, hydroxybenzoic, acrylic, methacrylic, thioacetic and thiopropionic acids and the $C_1$-$C_4$alkyl monoesters of terephthalic, phthalic, citric, maleic, fumaric, itaconic, malonic, succinic and thiosuccinic acids.

Preferred esters of the formula IIa are those wherein $R_1$ is a direct bond, —$CH_2$—, —$CH(CH_3)$—, —$CH_2CH_2$—O—$CH_2$—, —$CH_2CH_2$—S—$CH_2$—, —$CH$=$CHCH_2$—O—$CH_2$—, —$SO_2NR_o$—$CH_2$— or —$CONH$—$CH_2CH_2$—O—$CH_2$—, wherein $R_o$ is hydrogen or an alkyl group with 1 to 4 carbon atoms, $R_x$ is hydrogen or methyl, d is zero, $R_2$—CO— is the radical of acetic, benzoic, hydroxybenzoic, acrylic, methacrylic, thio-acetic or thio-propionic acid, or a $C_1$-$C_4$alkyl monoester of terephthalic, phthalic, citric, maleic, fumaric, itaconic, malonic, succinic or thiosuccinic acid and $R_F$ is saturated, contains 6–18 carbon atoms, is fully fluorinated and contains at least one terminal perfluoromethyl group. Of these, monomaleates and monosuccinates and mono-ortho- and terephthalates of the formula IIa, especially those wherein $R_1$ is —$CH_2$— and $R_x$ is hydrogen are especially preferred.

Structurally, $R_3$ is the divalent radical residue of a dicarboxylic acid of the formula HOOC-$R_3$—COOH. Such dicarboxylic acids include oxalic, maleic, fumaric, malonic, succinic, glutaric, iraconic, adipic, pimelic, suberic, azelaic, sebacic, brassylie, octadecanedioic, dimer acid, 1,4-cyclohexanedicarboxylic, 4,4'-dicyclohexyl-1,1'-dicarboxylic, phthalic, isophthalic, terephthalic, methylphthalic, chlorophthalic, diphenyl-2,2'-dicarboxylic, diphenyl-4,4'-dicarboxylic, 1,4-naphthalene dicarboxylic, diphenylmethane-2,2'-dicarboxylic, diphenyl-methane-3,3'-dicarboxylic, diphenylmethane-4,4'-dicarboxylic acid and the like. Also included are compounds wherein $R_3$ is substituted by one or two carboxy groups and is derived, for example, from trimellitic anhydride, pyromellitic dianhydride or benzophenone tetracarboxylic acid dianhydride. Compounds of the formula IIb wherein $R_3$ is the divalent radical residue of maleic, succinic or adipic acid are preferred.

Also useful are polyesters containing units of the formula IIc

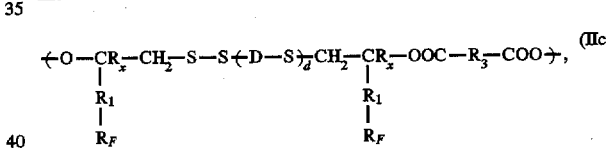

wherein $R_F$, $R_x$, $R_1$, $R_3$, D, and d are defined as above.

Preferably the polyesters of the formula IIc have molecular weights from about 3,000 to 30,000.

Preferred esters of the formulae IIb and IIc are those wherein $R_1$ is a direct bond, —$CH_2$—, —$CH(CH_3)$—, —$CH_2CH_2$—O—$CH_2$—, —$CH_2CH_2$—S—$CH_2$—, —$CH$=$CHCH_2$—O—$CH_2$—, —$SO_2NR_o$—$CH_2$— or —$CONH$—$CH_2CH_2$—O—$CH_2$—, wherein $R_o$ is hydrogen or an alkyl group with 1 to 4 carbon atoms, $R_x$ is hydrogen or methyl, d is zero, and $R_F$ is saturated, contains 6–18 carbon atoms, is fully fluorinated and contains at least one terminal perfluoromethyl group. Of these, esters wherein $R_1$ is —$CH_2$—, $R_x$ is hydrogen, —OOC—$R_3$—COO— is the diradical of maleic, succinic, or adipic acid and $R_F$ is a fully fluorinated, linear perfluoroalkyl group with 4 to 14 carbon atoms are especially preferred.

Also useful are carbonates derived from a bischloroformate, e.g. ethylene glycol bischloroformate.

Useful phosphates are of the formula III

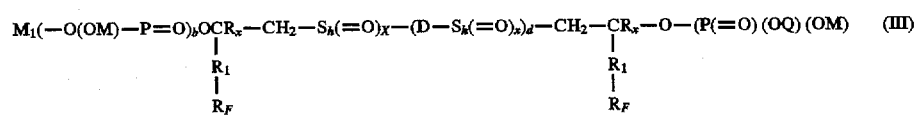

wherein Q is

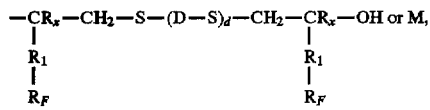

b is one or zero, M and $M_1$ are hydrogen, ammonium, $C_1$-$C_5$alkyl- or $C_1$-$C_5$hydroxyalkyl-substituted ammonium or an alkali metal cation, and $R_F$, $R_1$, $R_x$, D and d are defined as above, with the proviso that when b is zero, $M_1$ is hydrogen.

Preferred are phosphates wherein $R_1$ is a direct bond, —$CH_2$—, —$CH(CH_3)$—, —$CH_2CH_2$—O—$CH_2$—, —$CH_2CH_2$—S—$CH_2$—, —CH=CHCH$_2$—O—$CH_2$—, —$SO_2NR_o$—$CH_2$— or —CONH—$CH_2CH_2$—O—$CH_2$—, wherein $R_o$ is hydrogen or an alkyl group with 1 to 4 carbon atoms, d is zero, $R_x$ is hydrogen or methyl and $R_F$ is saturated, contains 6–18 carbon atoms, is fully fluorinated and contains at least one terminal perfluoromethyl group. Especially preferred are phosphates wherein $R_1$ is —$CH_2$—, $R_x$ is hydrogen and $R_F$ is a fully fluorinated, linear perfluoroalkyl group with 4 to 14 carbon atoms.

Useful sulfates are of the formula IV

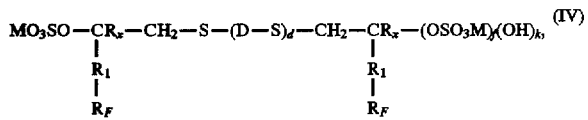

wherein one of f and k is zero and the other is 1, and M, $R_F$, $R_1$, $R_x$ d and D are defined as above.

Preferred are sulfates wherein $R_1$ is a direct bond, —$CH_2$—, —$CH(CH_3)$—, —$CH_2CH_2$—O—$CH_2$—, —$CH_2CH_2$—S—$CH_2$—, —CH=CHCH$_2$—O—$CH_2$—, —$SO_2NR_o$—$CH_2$— or —CONH—$CH_2CH_2$—O—$CH_2$—, wherein $R_o$ is hydrogen or an alkyl group with 1 to 4 carbon atoms, k is 1, d and f are zero, D is —$CH_2CH_2$—O—$CH_2CH_2$— or pentaerythritol diacetate or dipropionate, $R_x$ is hydrogen or methyl and the $R_F$ group is saturated, contains 4–18 carbon atoms, is fully fluorinated and contains at least one terminal perfluoromethyl group. Especially preferred are sulfates wherein $R_1$ is —$CH_2$—, $R_x$ is hydrogen, d and f are zero and $R_F$ is a fully fluorinated, linear perfluoroalkyl group with 4 to 14 carbon atoms.

Useful urethanes are the reaction products of a diol of the formula I with an isocyanate of the formula $R_4$-NCO, wherein $R_4$ is the monovalent hydrocarbon radical of phenyl isocyanate, m-isopropenyl-methyl benzyl isocyanato (TMI), 2-isocyanatoethyl acrylate or methacrylate (IEM) or 1,1-dimethyl-2-isocyanatoethyl-m-isopropenylphenyl.

Useful polyurethanes consist of or contain repeating units of the general formula V

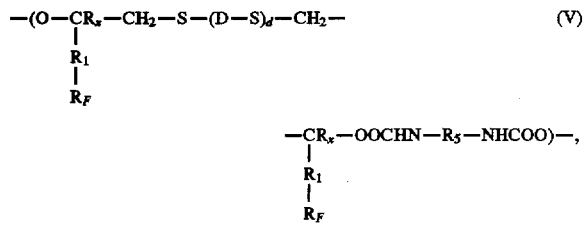

wherein $R_F$, $R_x$, $R_x$, D and d are defined as above, and $R_5$ is the diradical residue of a diisocyanate of the formula OCN-$R_5$-NCO.

Preferred polyurethanes are those wherein $R_1$ is a direct bond, —$CH_2$—, —$CH(CH_3)$—, —$CH_2CH_2$—O—$CH_2$—, —$CH_2CH_2$—S—$CH_2$—, —CH=CHCH$_2$—O—$CH_2$—, —$SO_2NR_o$—$CH_2$— or —CONH—$CH_2CH_2$—O—$CH_2$—, wherein $R_o$ is hydrogen or an alkyl group with 1 to 4 carbon atoms, $R_x$ is hydrogen or methyl and d is zero, and the $R_F$ group is saturated, contains 4-18 carbon atoms, is fully fluorinated and contains at least one terminal perfluoromethyl group and the group $R_5$ is aromatic, aliphatic or cycloaliphatic.

Useful aromatic diisocyanates include toluene diisocyanate CIDD (all isomers), 4,4'-diphenylmethane diisocyanate (MDD, tolidine diisocyanate, dianisidine diisocyanate, m-xylylene diisocyanate, p-phenylene diisocyanate, m-phenylene diisocyanate, 1-chloro-2,4-phenylene diisocyanate, 3,3'-dimethyl-4,4'-bisphenylene diisocyanate, 4,4'-bis(2-methyl-isocyanatophenyl)methane-4,4'-bisphenylene diisocyanate, 4,4'-bis(2-methoxyisocyanatophenyl)methane, 1-nitrophenyl-3,5-diisocyanate, 4,4'-diisocyanatodiphenyl ether, 3,3'-dichloro-4,4'-diisocyanatodiphenyl ether, 3,3'-dichloro-4,4'-diisocyanatodiphenyl-methane, 4,4'-diisocyanatodibenzyl, 3,3'-dimethoxy-4,4'-diisocyanatodiphenyl, 2,2'-dimethyl-4,4'-diisocyanatodiphenyl, 2,2'-dichloro-5,5'-dimethoxy-4,4'-diisocyanato-diphenyl, 3,3'-dichloro-4,4'-diisocyanatodiphenyl, 1,2-naphthalene diisocyanate, 4-chloro-1,2-naphthalene diisocyanate, 4-methyl-1,2-naphthalene diisocyanate, 1,5-naphthalene diisocyanate, 1,6-naphthalene diisocyanate, 1,7-naphthalene diisocyanate, 1,8-naphthalene diisocyanate, 4-chloro-1,8-naphthalene diisocyanate, 2,3-naphthalene diisocyanate, 2,7-naphthalene diisocyanate, 1,8-dinitro-2,7-naphthalene diisocyanate, 1-methyl-2,4-naphthalene diisocyanate, 1-methyl-5,7-naphthalene diisocyanate, 6-methyl-1,3 -naphthalene diisocyanate and 7-methyl- 1,3-naphthalene diisocyanate.

Useful aliphatic or cycloaliphatic polyisocyanates include 1,2-ethane diisocyanate, propylene-1,2- and-1,3 diisocyanate, 1,4-tetramethylene diisocyanate, 2-chloropropane-1,3-diisocyanate, pentamethylene diisocyanate, 1,8-octane diisocyanate, 1,10-decane diisocyanate, 1,12-dodecane, 1,16-hexadecane diisocyanate and other aliphatic diisocyanates such as 1,3-cyclohexane diisocyanate and 1,4-cyclohexane diisocyanate.

Additionally, the following diisocyanates are particularly preferred because urethane compositions made therefrom tend to be non-yellowing: 1,6-hexamethylene diisocyanate (HDI), 2,2,4- and 2,4,4-trimethyl-1,6-diisocyanatohexane (TMDI), dimer acid-derived diisocyanate (DDI), obtained from dimerized fatty acids such as linoleic acid, 4,4'-dicyclo-hexylmethane diisocyanate (hydrogenareal MDI), isophorone diisocyanate, 3-isocyanato-methyl-3,5,5-trimethylcyclohexyl diisocyanate, lysine methyl ester diisocyanate (LDIM), bis(2-isocyanatoethyl) fumarate (FDI), bis (2-isocyanatoethyl) carbonate and m-tetramethyl-xylylene diisocyanate (TMXDI).

Especially preferred are polyurethanes wherein $R_1$ is —$CH_2$—, $R_x$ is hydrogen, d is zero, and $R_F$ is saturated and contains 6–18 carbon atoms, is fully fluorinated and contains at least one terminal perfluoromethyl group, and $R_5$ is the diradical residue of isophorone diisocyanate, 2,2,4(2,4,4)-trimethyl-1,6-diisocyanatohexane, linoleic dimer acid-derived diisocyanate, 1,6-hexamethylene diisocyanate or 3-isocyanatomethyl-3,5,5-trimethylcyclohexyl diisocyanate.

It is preferred that the polyurethanes have molecular weights from about 3,000 to 30,000.

Esters of the formulae IIa-IIc and carbonates may be prepared by reacting diols of formula I with acid chlorides, esters or chloroformales to yield carboxylate esters and carbonates respectively. For example, acetyl chloride can be reacted with a diol of formula I to give an acetate derivative. This reaction is preferably carried out in the presence of an organic amine to scavenge HCl.

Sulfate esters are prepared by the reaction of the inventive diols with chlorosulfonic acid or, preferably, with sulfamic acid in the presence of a base or a basic solvent such as pyridine, N-methylpyrrolidone, urea or tetramethylurea. This reaction is usually carried out at about 100°–105° C. for 2 to 10 hours. The advantage of using sulfamic acid rather than chlorosulfonic acid is the direct formation of an ammonium salt in a single step.

The reaction of a diol of formula I with polyphosphoric acid or $POCl_3$ will give a phosphate ester of the formula III. This reaction is typically carried out at about 85° C. using glyme as solvent. These phosphates are usually reacted with a base such as ammonia to convert them to the corresponding ammonium salts for water solubility and for application testing.

Polyurethanes are prepared from the diols of this invention by the known methods of polyurethane chemistry. These polyurethanes may also contain other building blocks derived from commercially available diols or diamines, especially tertiary amino group-containing diols such as N-methyldiethanolamine, polyethylene oxide diols and 3-aminopropyl-terminated polyethylene oxide (Jeffamine-ED, from TEXACO Corp.), poly-(dimethylsiloxane)-dialkanols and poly-(dimethylsiloxane)-dialkylamino. Typical polyurethane compositions incorporating known diols and diamines in combination with certain other perfluoroalkyl-substituted diols are described for example in U.S. Pat. Nos. 3,968,066, 4,046,944 and 4,098,742.

Also, this invention relates to a substrate containing 0.01 to 10% by weight of a fluorine-containing composition, at least part of said fluorine being provided by one or more compounds derived from an $R_F$-diol of formula I. Such substrates include glass, wood, paper, leather, textiles such as nylon, wool, cotton, polyester, and other substrates. The above reaction products and their further derivatives of the diols of formula I impart oil and water repellency to said substrates. Said substrates and methods of preparing them are further objects of this invention.

The following examples are intended for illustrative purposes only, and are not intended to restrict the scope of the invention in any way.

Example 1

Synthesis of a 2-iodo-3-perfluoroalkyl-1-propanol.

Into a 1 l round-bottomed-flask equipped with condenser, thermometer, stirrer and a nitrogen gas inlet tube are charged 606.0 g (1.0 mole) of a perfluoroalkyl iodide ($R_F$I) with a homologue distribution of 1.7% $C_6$, 49.8% $C_8$, 33.5% $C_{10}$, 11.1% $C_{12}$, 3.1% $C_{14}$, 0.69% $C_{16}$ and 0.16% $C_{18}$, (Telomer-AN, from DuPont), 22.6 g $H_2O$ (1.26 mole) and 14.8 g sodium metabisulfite ($Na_2S_2O_5$ 0.078 mole). The mixture is heated on an oil bath to 80° C. with stirring. After the addition of 2.88 g (0.015 mole) 2,2'-azo-bis-(2-methylbutyronitrile) (VAZO-67, from WAKO Chem. Co.), 112.8 g allyl alcohol (1.16 mole) as a 60% solution in water are continuously added over 210 minutes using a Masterflex pump at a flow rate of 32.2 g/h. A small temperature increase of the reaction mass is observed. Product formation was followed by monitoring the decrease of $R_F$I concentration via gas chromatography. No substantial accumulation of $R_F$I is seen, i.e. the allyl alcohol reacts immediately upon addition.

After 210 minutes, the addition rate of the aqueous allyl alcohol solution is increased to 102 g/h for the following two hours. The total mount of allyl alcohol solution used in the reaction is 318.2 g, corresponding to a molar ratio of $R_F$I to allyl alcohol=1.0:3.28. The total amount of water used is 31.5%, based on $R_F$I.

The formed 2-iodo-3-perfluoroalkyl-1-propanol is obtained as a solution in the excess of aqueous allyl alcohol. The excess allyl alcohol is distilled off in vacuo and the product is filtered off, rinsed with deionized water and dried in vacuo at 50° C. It is obtained as a dark-yellow waxy solid in 98% yield; the conversion of $R_F$I is 100%.

Example 2

Heptane-1,7-di-perfluoroalkyl-4-thia-2,6-diol.

Into a 300 ml, three neck round-bottomed flask are placed the 2-iodo-3-perfluoroalkyl-1-propanol of Example 1 (70 g, 0.105 mol), 26 g water, 17 g ethanol and 8.6 g methyl propyl ketone (MPK). The mixture is stirred at 42° C. and solid $Na_2Sx9H_2O$ (126 g, 0.053 mol) is added over a 30 minute period. After the addition is completed, the reaction mixture is heated to 55° C. The progress of the reaction is monitored by gas chromatography. After one hour the reaction is complete. The MPK is distilled off at 80° C., whereupon the mixture separates into two phases. The aqueous phase is removed and the organic phase is washed twice with 10% HCl. Small amounts of residual MPK are removed under vacuum. A light yellow crystalline material is obtained and dried in vacuum (45° C.) to give 110 g (95% yield) of the tide di-$R_F$-diol with a melting point, m.p., of 118° C.

The structure is confirmed by H-NMR ($CDCl_3$, 500 MHz): d 4.3 (2H, bs, -CHOH), 2.7 and 2.9 (4H, m, —$CH_2$S—) and 2.4 (4H, m, $R_F$$CH_2$—).

Example 3

Heptane-1,7-di-perfluoroalkyl-4-thia-2,6-diol; preparation from a perfluoroalkyl-propylene oxide.

Into a 2 l three-neck round-bottomed flask equipped with a mechanical stirrer are poured melted $C_9$-$C_{21}$-perfluoroalkyl-propylene oxide (ZONYL-TE; DuPont Chem. Corp.) (559.0 g, 0.98 mol) and 38 ml acetone. This mixture is stirred at 43° C. until it turns clear. To this mixture is added a solution of $Na_2Sx9H_2O$ (120.1 g, 0.49 mol) in 135 ml water over a 50 minute period. During the addition the temperature of the reaction mixture is maintained at about 43° C. by using a cooling bath. After the addition of $Na_2Sx9H_2O$ is complete, the stirred yellow turbid mixture is heated at 55° C. for 2 hours. The progress of the reaction is monitored by gas chromatography. After 2 hours the reaction is complete. Acetone is removed from the reaction mixture by distillation at 78° C. and the remaining aqueous slurry is filtered. The filter cake is washed three times with 200 ml of cold water. Subsequent drying of the filter cake under vacuum gives 555.0 g (96.5% yield) of a tan powder with a m.p. of 118°–124° C. and a fluorine content of 63.4%

(Calculated: 63.2%). NMR data are identical to those obtained for Example 2.

Example 4

Synthesis of a polyurethane.

40.09 g (42.2 mmoles) of the heptane-1,7-di-perfluoroalkyl-4-thia-2,6-diol of Example 2 and 93.04 g isopropyl acetate are placed into a 250 ml 3-necked round-bottomed flask fitted with a mechanical stirrer, gas inlet, thermometer, Dean-Stark trap and condenser. The mixture is kept under nitrogen and heated to reflux to remove water as an azeotrope with the isopropyl acetate: 20 ml of distillate are collected in the trap.

The contents are cooled to 75° C. and 6.74 g (31.6 mmoles) of 2,2,4-trimethyl-1,6-diiso-cyanatohexane (TMDI) is added, followed by 0.10 g (0.16 mmoles) of dibutyltin dilaurate (DBTL). The flask contents are stirred for approximately one hour at 80° C., or until the TMDI content is below 0.2% as determined by IR.

15.62 g (26.4 mmoles) of dimer acid diisocyanate (DDI 1410, from Henkel Chemie) and 1.90 g (15.9 mmoles) of N-methyl diethanolamine (NMDEA) are added, followed by 26.2 g isopropyl acetate as a rinse. The mixture is stirred for 2 hours at 80° C. After this time no more NCO groups remain present as determined by IR-spectroscopy. The product polyurethane is obtained as a 40% solution in isopropyl acetate. It contains the diol, TMDI, DDI, and NMDEA in a mol ratio of 4:3:2.5:1.5. On drying, the polyurethane forms a clear tough, highly oil- and water-repellent film.

Example 5

The following example demonstrates the usefulness of a novel polyurethane as an oil and water-repellent textile finish.

Emulsification:

In 93.8 g water are dissolved 1.87 g Arquad-2C/75 (dicocodimethylammonium chloride, from Akzo Corp.) and 0.63 g Ethoquad 18/25 (methyl-polyoxyethyl(15)-octadecyl ammonium chloride, from Akzo Corp.) to make up the aqueous phase. The polyurethane solution of Example 4 is adjusted to 40% solids with isopropyl acetate, forming the organic phase. Both solutions are heated to 60°–70° C. Then 45 g of the polyurethane solution is added to the aqueous phase while stirring. This mixture is homogenized first with a high-shear stirrer (POLYTRON) for 2 minutes, followed by 2–3 passes through a MICROFLUIDIZER at 5000–7000 psi. The emulsion is then stripped free of organic solvent on a rotary evaporator at reduced pressure.

Application:

The polyurethane emulsion is formulated into a pad bath containing 6% by weight of the permanent press resin Permafresh-113B (Sequa Chem. Corp.), 1.2% Catalyst 531 ($Zn(NO_3)_2$) and an amount of polyurethane emulsion calculated to result in 0.12% fluorine in the bath. This mixture is applied to cotton fabric at 85% wet pick-up. The fabric is dried for 10 min. at 110° C. and cured for 5 min. at 150° C. The test results are shown in the table. They demonstrate excellent performance, even after repeated washing and drycleaning.

TEST METHODS:

The AATCC Water Spray test rating was determined according to Standard Test method 22-1985 of the American Association of Textile Chemists and Colorists, Volume 61, 1986 (also designated ASTM-D-583-58). Ratings are given from 0 (minimum) to 100 (maximum).

The AATCC Oil Rating was determined according to Standard Test method 118-1983 of the American Association of Textile Chemists and Colorists. Ratings are given from 0 (minimum) to 8 (maximum). A commonly accepted level of repellency for oil-repellent coatings in the United States is an oil repellency of 4.

The Bundesmann test simulates the conditions of a fabric being worn during a heavy rain. In this test water absorption is measured in percent pick-up, (underlined numbers in the following table) and appearance (3 samples), rated from 1 (lowest) to 5 (highest rating).

| TEST RESULTS | | | |
|---|---|---|---|
| | oil kit | spray | Bundesmann |
| initial | 6 | 3 × 100 | <u>11</u>; 5, 5, 5 |
| 5 × 60° wash | 5 | 3 × 80 | <u>23</u>; 2, 1, 1 |
| 1 × dryclean | 4 | 100, 90, 90 | <u>27</u>; 5, 3, 2 |

Example 6

This example illustrates the synthesis of di-perfluoroalkyl sulfate esters by reaction of a heptane-1,7-di-perfluoroalkyl-4-thia-2,6-diol with sulfamic acid.

Into a 100 ml round-bottomed flask are placed the heptane-1,7-di-perfluoroalkyl-4-thia-2,6-diol of Example 2 (19.4 g, 0.0150 mol), sulfamic acid (2.62 g, 0.027 mol) and 5.0 g of tetra-methylurea. This mixture is stirred under nitrogen for 1.5 hours at 103° C. The progress of the reaction and the final degree of sulfation is monitored by a two-phase titration of the forming di-perfluoroalkyl sulfate ammonium salt with benzethonium chloride solution according to the procedure described in "Analysis of Surfactants", Surfactant Sci. Series, Vol. 40, (Marcel Decker Inc., New York, 1992).

The final degree of sulfation, expressed as OH equiv$_{initial}$ / OH equiv$_{final}$, is 0.85.

The product is dissolved in water and used for application tests.

Example 7

The following example demonstrates the usefulness of the sulfate ester-acids as oil-repellent paper sizes.

SAMPLE PREPARATION AND TESTING:

External Size Application:

Samples of the product of Example 6 are diluted to the test application levels with distilled water. The solutions are added to a 4% aqueous solution of paper maker's starch (Stayco M, oxidized starch, from Staley Corp.) and then applied to unsized paper by padding (paper dipped through starch solution, and passed through single nip rollers). The resulting sheets are dried at ambient conditions for 15 minutes, then 3 minutes at 200° F. in an "Emerson Speed Drier" (heated metal plate with canvas cover).

Oil Kit Test:

The oil repellency of the surface is determined by using the TAPPIUM 557 OIL KIT TEST, which consists of determining which of twelve Castor oil-heptane-toluene mixtures having decreasing surface tension causes penetration to occur within 15 seconds: ratings go from 1 (lowest) to 12.

Grease Resistance Test:

Grease resistance is determined with the Ralston-Purina RP-2 test for pet food materials; Ralston-Purina Company, Packaging Reference Manual Volume 06 - Test Methods.

In summary; cross-wise creased test papers are placed over a grid sheet imprinted with 100 squares. Five grams of sand are placed in the center of the crease. A mixture of synthetic oil and a dye for visualization is pipetted onto the sand and the samples are maintained at 60° C. for 24 hours. Ratings are determined by the percentage of stained grid segments on at least two samples.

Internal Size Application and Testing:

Six grams of dry recycled pulp consisting of ≈70% hard-wood and 30% soft-wood are diluted in 289 ml distilled water and thoroughly dispersed in a blender. To this pulp slurry is added a 1% dilution (as is) of the test dispersion in distilled water and mixed in for 5 minutes. Then 6 ml of a 1% aqueous solution of cooked cationic starch is added and mixed together for an additional 5 minutes. To this 24 ml of a 50% (on solids) dilution of a water-repellent adjuvant (Hercon-76, from Nalco Chem. Corp.) are added and mixed in for another 10 minutes. The resulting slurry is diluted with an additional 500 ml of distilled water and mixed again. This mixture is then poured over a 100 mesh wire screen, with a vacuum applied from below which pulls the water from the pulp mixture to form a sheet on the screen. The wet sheet is removed from the screen and dried between another screen and a hard surface at a pressure of approximately 0.4 lb./in$^2$ at 110° C. for 1½ hours.

Hot-Oil Test:

One ml of hot (110° C.) corn oil is placed on the paper and the time is noted for penetration to occur (20 min. maximum). Paper made in the same manner as above, including the cationic starch and water repellent adjuvant but without a fluorochemical of this invention, demonstrates an oil kit number of <1. It holds the hot corn oil for less than one minute (begins to penetrate as soon as applied).

The amount of oil absorbed is determined gravimetrically by weighing the paper before and after the hot oil test, after the surface oil has been removed.

The Oil-Kit Test is the same as that for the External Size.

The test results are shown in the following table:

| Ex. No. 7 | % F | External Size oil kit | RP-2 test | Internal Size Hold-out oil kit | time (min.) | % oil absorbed |
|---|---|---|---|---|---|---|
| Compound of Example 6 | 0.05 | 5 | 2 × 0 | 3 | <3 | 44 |
|  | 0.07 | 7 | 2 × 0 | 4 | >20 | 0 |
|  | 0.10 | 10 | 2 × 0 | 5 | >20 | 0 |

Example 8

Conversion of a sulfur diol to a sulfone.

A 100 ml single-necked, round-bottomed flask equipped with a stirring bar and cold water condenser is charged with 19.0 g (0.32 mol) glacial acetic acid and 25.0 g (0.025 mol) of the diol of Example 3. With good stirring, the diol is dissolved by heating to 40° C. and 2.9 g (0.08 mol, 34%) hydrogen peroxide is added, during which the mixture turns dark amber. After one hour, the reaction mixture is heated to 100° C. and an additional 5.7 g (0. 17 mol, 34%) hydrogen peroxide are charged. After 3 hours the product mixture is poured into 1 liter of crushed ice and water, filtered through a Buchner funnel, washed several times with cold water, and dried under vacuum to provide 25.2 g (91%) of tan crystals with a melting point of 125°–128° C.; the structure is confirmed by NMR: (DMF-D$_7$, 500 MHz) d: 5.8 (2H, bs, —O$\underline{H}$—), 4.6 (2H, m, —C$\underline{H}$(OH)—), 3.2 (4H, m, —C$\underline{H}_2$SO$_2$—), 2.8–2.4 (4H, m, —CF$_2$C$\underline{H}_2$—).

Example 9

Synthesis of a disulfide diol.

The 2-iodo-3-perfluoroalkyl-1-propanol of Example 1, 13.3 g (26 mmol, in 6 g ethanol is magnetically stirred in a three-necked round-bottomed flask at 54° C. A solution of 2.4 g (90%, 12.4 mmol) sodium tetrasulfide, 2 g ethanol and 2.3 g water are added through an addition funnel over 30 minutes to give a thick, yellow, paste. After holding for one hour at 54° C., the temperature is raised to 75° C. and held there for 5 hours. GC analysis at this time shows 85% conversion of the 2-iodo-3-perfluoroalkyl-1-propanol. The product mixture is evaporated to dryness and washed with cold, slightly acidic deionized water to give 11.1 g (92%) of a gray solid. Analysis by GC/MS of the crude mixture shows instead of the tetrasulfide the disulfide of the formula:

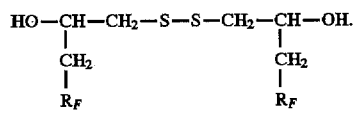

Example 10

Synthesis of a di-thioether diol.

The 2-iodo-3-perfluoroalkyl-1-propanol of Example 1 (10 g, 15 mmol) in 10 g ethanol are magnetically stirred at 49° C. in a 50 ml three-necked, round-bottomed flask. To this solution is added through a dropping funnel over 35 minutes a solution of 1.1 g (95%, 7.5 mmol) di(2-mercaptoethyl) ether, 3.0 g (50%, 1.6 mmol) sodium hydroxide and 4.1 g ethanol to give an off-white paste. Next 5.8 g acetone is added and the solution is stirred at 49° C. for 2 hours, then refluxed at 76° C. for one hour. The product mixture is evaporated to dryness under reduced pressure at 65° C. on a rotary evaporator. The resulting cake is stirred in 500 ml of ice cold diluted HCl (pH<3), filtered through a Buchner funnel and dried under reduced pressure at 60° C. GC analysis of the yellow solid (8,4 g, 95%, m.p. 95°–107° C.) shows complete conversion of the 2-iodo-3-perfluoroalkyl-1-propanol to product. The structure of the product,

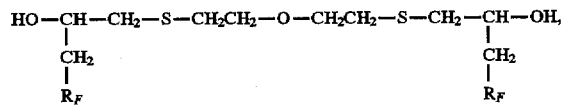

is confirmed by GC/MS.

What is claimed is:

1. A polyurethane having a molecular weight of from about 3,000 to 30,000 which consists of or contains repeating units of the formula V

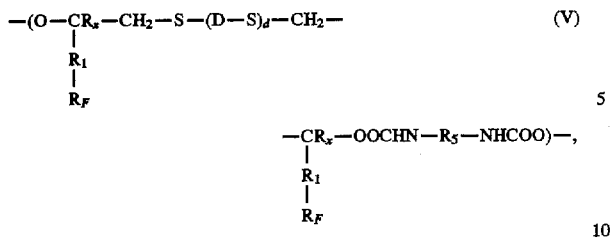

wherein

R$_x$ is hydrogen or methyl,

R$_5$ is aromatic, aliphatic or cycloaliphatic

R$_1$ is a direct bond, a linear or branched alkylene of up to 6 carbon atoms, alkyleneoxyalkylene of up to 6 carbon atoms, alkylenethioalkylene of up to 6 carbon atoms, alkyleneoxy of up to 6 carbon atoms, alkenyleneoxyalkylene of up to 6 carbon atoms, alkylenethioalkyleneoxyalkylene of up to 9 carbon atoms, carbonamidoalkylene where the alkylene moiety contains up to 6 carbon atoms and the amido nitrogen is unsubstituted or further substituted by lower alkyl, sulfonamidoalkylene wherein the alkylene moiety contains up to 6 carbon atoms and the amido nitrogen is unsubstituted or further substituted by lower alkyl; carbonamidoalkylenethioalkylene wherein the carbonamidoalkylene moiety is as defined hereinabove and the thioalkylene moiety contains up to 6 carbon atoms, or sulfonamidoalkylenethioalkylene wherein the sulfonamidoalkylene moiety is as defined hereinabove and the thioalkylene moiety contains up to 6 carbon atoms, d is 0 or 1, D is an alkylene group with 2 to 10 carbon atoms, a dialkylene ether group with 4 to 10 carbon atoms, or pentaerythritol diacetate or dipropionate, and R$_F$ is a monovalent, perfluorinated, alkyl or alkenyl, straight, branched or cyclic, organic radical having 3 to 20 fully fluorinated carbon atoms, which radical can be interrupted by one or more divalent oxygen or sulfur atoms, and each R$_F$ radical is the same or different.

2. A polyurethane according to claim 1, wherein

R$_1$ is a direct bond, —CH$_2$—, —CH(CH$_3$)—, —CH$_2$CH$_2$—O—CH$_2$, —CH$_2$CH$_2$—S—CH$_2$—, —CH=CHCH$_2$—O—CH$_2$—, —SO$_2$NR$_o$—CH$_2$- or CONH-CH$_2$CH$_2$—O—CH$_2$—, wherein R$_o$ is hydrogen or an alkyl group with 1 to 4 carbon atoms, d is zero, the R$_F$ group is saturated, contains 4–18 carbon atoms, is fully fluorinated and contains at least one terminal perfluoromethyl group and R$_5$ is the diradical residue of a diisocyanate of the formula OCN-R$_5$-NCO selected from the group consisting of toluene diisocyanate, 4,4'-diphenylmethane diisocyanate, tolidine diisocyanate, dianisidine diisocyanate, m-xylylene diisocyanate, p-phenylene diisocyanate, m-phenylene diisocyanate, 1-chloro-2,4-phenylene diisocyanate, 3,3'-dimethyl-4,4'-bisphenylene diisocyanate, 4,4'-bis(2-methylisocyimatophenyl)methane-4,4'-bisphenylene diisocyanate, 4,4'-bis(2-methoxyisocyanatophenyl)methane, 1-nitrophenyl-3,5-diisocyanate, 4,4'-diisocyanatodiphenyl ether, 3,3'-dichloro-4,4'-diisocyanatodiphenyl ether, 3,3'-dichloro-4,4'-diisocyanatodiphenylmethane, 4,4'-diisocyanatodibenzyl, 3,3'-dimethoxy-4,4'-diisocyanatodiphenyl, 2,2'-dimethyl-4,4'-diisocyanatodiphenyl, 2,2'-dichloro-5,5'-dimethoxy-4,4'-diisocyanatodiphenyl, 3,3'-dichloro-4,4'-diisocyanato-diphenyl, 1,2-naphthalene diisocyanate, 4-chloro-1,2onaphthalene diisocyanate, 4-methyl-1,2-naphthalene diisocyanate, 1,5-naphthalene diisocyanate, 1,6-naphthalene diisocyanate, 1,7-naphthalene diisocyanate, 1,8-naphthalene diisocyanate, 4-chloro-1,8-naphthalene diisocyanate, 2,3-naphthalene diisocyanate, 2,7-naphthalene diisocyanate, 1,8-dinitro-2,7-naphthalene diisocyanate, 1-methyl-2,4-naphthalene diisocyanate, 1-methyl-5,7-naphthalene diisocyanate, 6-methyl-1,3-naphthalene diisocyanate, 7-methyl-1,3-naphthalene diisocyanate, 1,2-ethane diisocyanate, propylene-1,2- and -1,3 diisocyanate, 1,4-tetramethylene diisocyanate, 2-chloropropane-1,3-diisocyanate, pentmethylene diisocyanate, 1,8-octane diisocyanate, 1,10-alecane diisocyanate, 1,12-dodecane diisocyanate, 1,16-hexadecane diisocyanate, 1,3-cyclohexane diisocyanate, 1,4-cyclohexane diisocyanate, 4,4'-methylenebis(cyclohexyl isocyanate), 1,6-hexamethylene diisocyanate, 2,2,4- and 2,4,4otrimethyl- 1,6-diisocyanatohexane, dimer acid-derived diisocyanate obtained from dimerized linoleic fatty acid, 4,4'-dicyclohexylmethane diisocyanate, isophorone diisocyanate, 3-isocyanatomethyl-3,5,5-trimethylcyclohexyl diisocyanate, lysine methyl ester diisocyanate, bis(2-isocyanatoethyl) fumarate, bis(2-isocyanatoethyl) carbonate and m-tetramethylxylylene diisocyanate.

3. A polyurethane according to claim 2, wherein R$_1$ is —CH$_2$—, R$_x$ is hydrogen, d is zero, and R$_F$ is saturated and contains-6–18 carbon atoms, is fully fluorinated and contains at least one terminal perfluoromethyl group, and R$_5$ is the diradical residue of isophorone diisocyanate, 2,2,4(2,4,4)-trimethyl-1,6-diisocyanatohexane, linoleic dimer acid-derived diisocyanate, 1,6-hexamethylene diisocyanate or 3-isocyanatomethyl-3,5,5-trimethylcyclohexyl diisocyanate.

4. A method of treating a substrate to impart oil and water repellency to it, which comprises applying an effective amount of a fluorine-containing composition thereto, wherein at least part of the fluorine in said composition is provided by one or more compounds selected from the group consisting of polyurethanes having molecular weights of from about 3,000 to 30,000 and consisting of or containing repeating units of the formula V

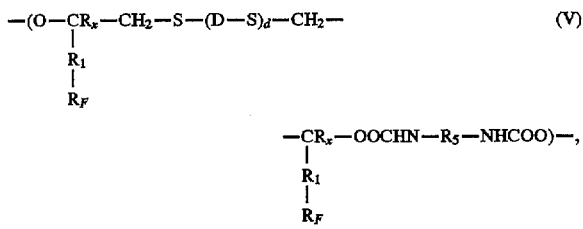

wherein R$_F$, R$_x$, R$_x$, D, d and R$_5$ are as defined in claim 1.

* * * * *